United States Patent
Teixeira Rangel

(10) Patent No.: US 12,193,917 B2
(45) Date of Patent: Jan. 14, 2025

(54) WEARABLE LIQUID SILICONE RUBBER PRODUCT

(71) Applicant: Ana Maria Teixeira Rangel, Norcross, GA (US)

(72) Inventor: Ana Maria Teixeira Rangel, Norcross, GA (US)

(*) Notice: Subject to any disclaimer, the term of this patent is extended or adjusted under 35 U.S.C. 154(b) by 163 days.

(21) Appl. No.: 17/888,085

(22) Filed: Aug. 15, 2022

(65) Prior Publication Data

US 2022/0401267 A1    Dec. 22, 2022

Related U.S. Application Data

(63) Continuation-in-part of application No. 17/399,885, filed on Aug. 11, 2021, now Pat. No. 11,412,788, which is a continuation of application No. 17/428,399, filed as application No. PCT/BR2021/050141 on Apr. 7, 2021.

(51) Int. Cl.
*A41D 13/015* (2006.01)
*A41D 13/06* (2006.01)
*A61F 13/06* (2006.01)

(52) U.S. Cl.
CPC .......... *A61F 13/061* (2013.01); *A41D 13/065* (2013.01)

(58) Field of Classification Search
CPC .. A41D 13/015; A41D 19/061; A41D 13/061; A41D 19/06; A41D 19/0062; A61F 2007/0225
See application file for complete search history.

(56) References Cited

U.S. PATENT DOCUMENTS

| | | | | |
|---|---|---|---|---|
| 909,215 | A | * | 10/1909 | Pierce et al. |
| 942,003 | A | * | 11/1909 | Marsh |
| 2,640,989 | A | * | 6/1953 | James ................. A41D 13/0568 2/22 |
| 3,602,917 | A | * | 9/1971 | Seunevel ............ A41D 19/0062 2/167 |
| 5,031,240 | A | * | 7/1991 | Nierhaus .............. A41D 13/065 2/24 |
| 5,269,322 | A | * | 12/1993 | Mandel ................. A61F 5/3715 128/845 |
| 5,323,490 | A | * | 6/1994 | Yarbrough ......... A41D 19/0062 2/163 |

(Continued)

*Primary Examiner* — Tajash D Patel

(74) *Attorney, Agent, or Firm* — Johnson | Dalal; Mark C. Johnson

(57) ABSTRACT

A cured liquid silicone rubber ("LSR") body having an outer surface, an inner surface opposing the outer surface, a first end, a second end opposing the first end, a non-biased body length separating the first and second ends of the cured silicone body, a pre-formed pleated portion disposed circumferentially along the body length and operably configured to enable selective and elastically biased adjustment of the non-biased body length, non-pleated portions of the LSR body forming a smooth surface of the outer surface of the LSR body and flanking the pleated portion, forming a sleeve shape with at least one enclosed opening and a sleeve channel for receiving a user's limb and defined by the inner surface of the LSR body, and defining a plurality of perforations thereon, disposed on the non-pleated portions of the LSR body that span through the LSR body.

3 Claims, 18 Drawing Sheets

(56) References Cited

U.S. PATENT DOCUMENTS

| | | | | |
|---|---|---|---|---|
| 5,592,953 | A | * | 1/1997 | Delao ................... A61F 15/004 |
| | | | | 128/882 |
| 6,694,594 | B2 | * | 2/2004 | Chung ................... B23P 15/00 |
| | | | | 29/421.1 |
| 11,412,788 | B2 | * | 8/2022 | Teixeira Rangel .. A41D 13/015 |

* cited by examiner

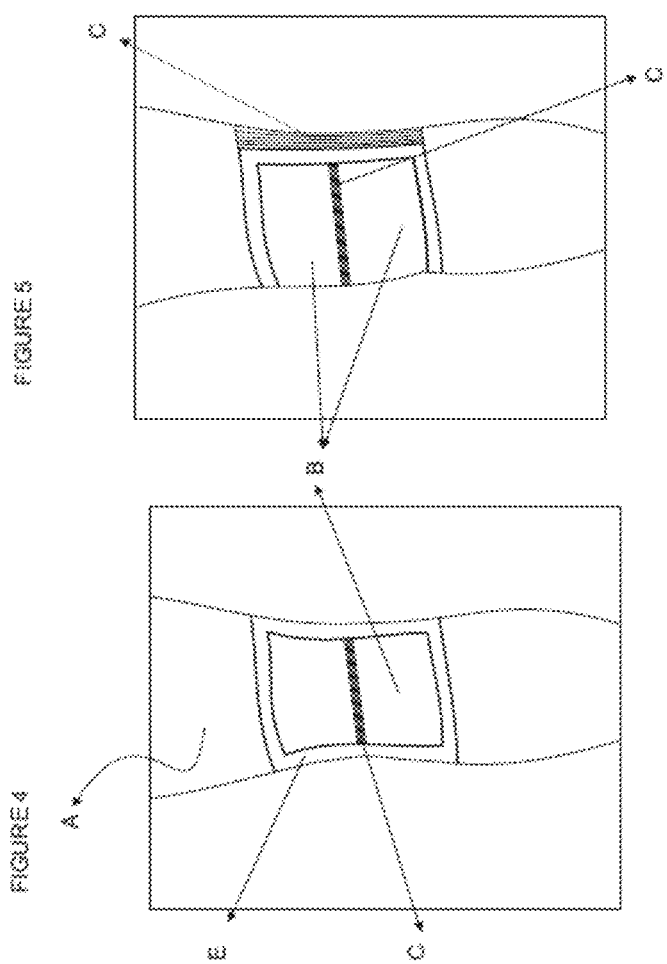

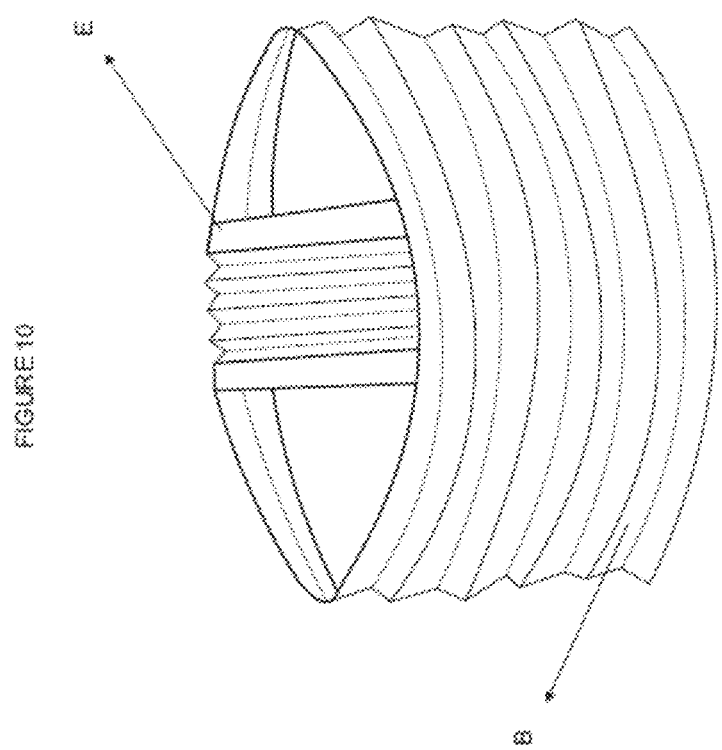

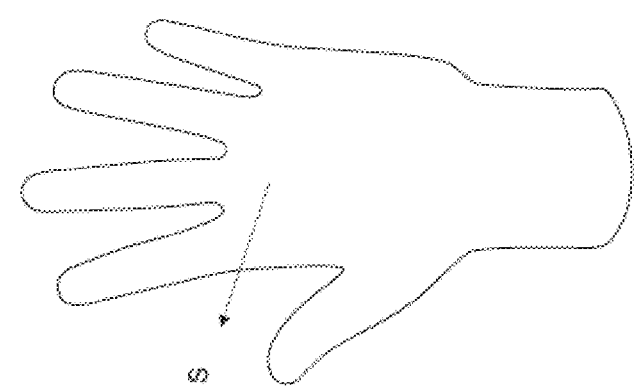
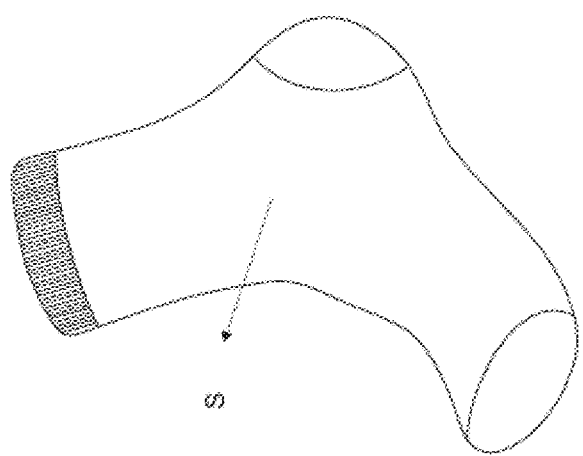
FIGURE 14

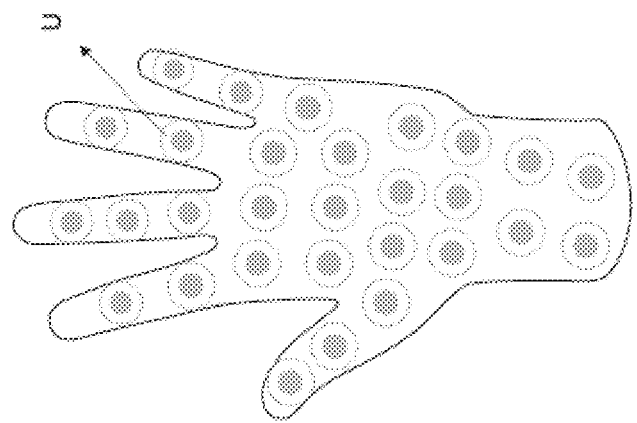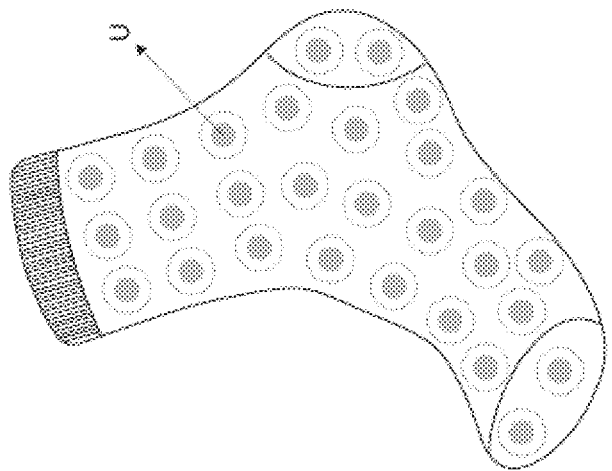
FIGURE 15

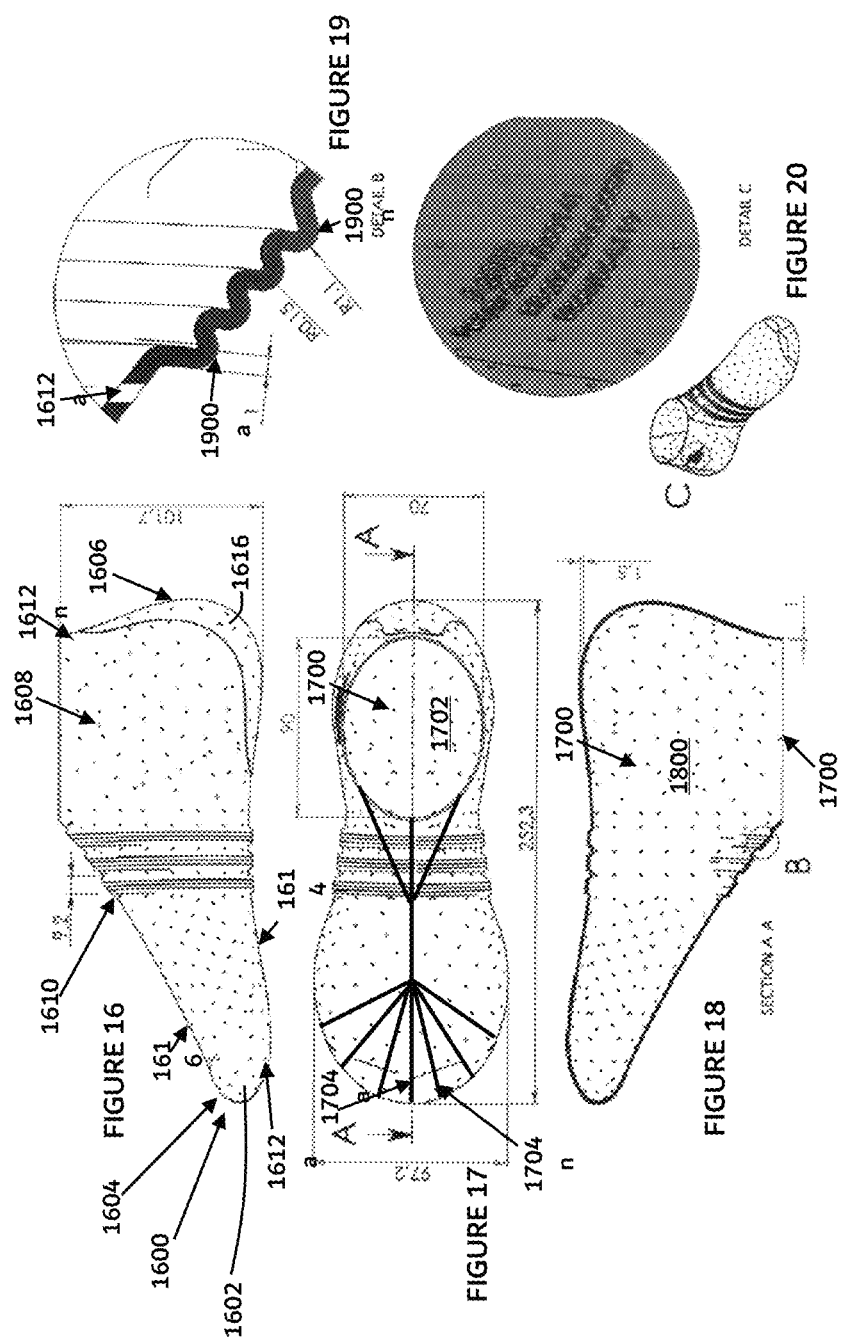

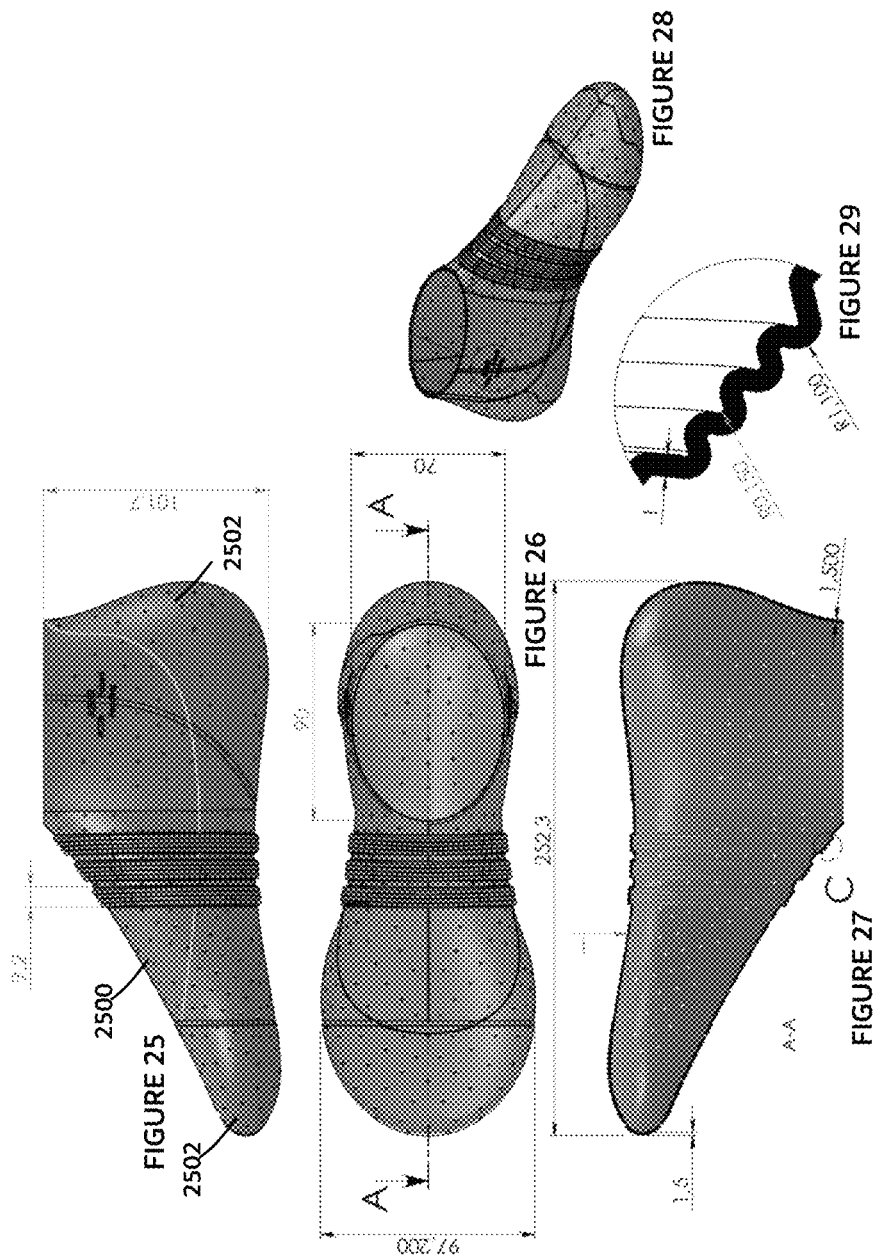

WEARABLE LIQUID SILICONE RUBBER PRODUCT

FIELD OF THE INVENTION

The present invention relates generally to objects form with silicone and more particularly relates to cured liquid silicone rubber (LSR) to be used in the field of clothing and personal care accessories, trimmings, products to cover, protect, treat, and rehabilitate the user's body parts during activities daily or rest, in different weather conditions and environments, as well as during sporting events, games, training or physical activities in general.

BACKGROUND OF THE INVENTION

In recent years, manufacturers clothing and protective equipment, and production sought to provide varying levels of comfort, protection, and functionality together with specific types of protective accessories, using different materials, knitting/sewing and other techniques in an attempt to not harm the skin.

In the current state of the art, several known products relate to the silicone material that comes in contact with the skin. One known product relates to articles that include garments with at least one opening layer included, wherein the articles may include an elastic polymer composition, such as a film, a molten material, or an aqueous dispersion. Another known product includes a sleeve and device with graduated compression for the treatment and/or prevention of lymphedema, which refers to a therapeutic sleeve made of mesh fabric with graduated compression with features multifunctional and that favors conditions to prevent the appearance or worsening of lymphoedema in the limbs. As such, swelling in the limbs and increased comfort is prevented, including thermo physiological, ergonomic, and psychological of the user during use.

Another known product includes a garment with a portion of knitted welt extending circumferentially, having an anti-slip zone comprising a high wire friction contact the user's skin to increase the anti-slip properties of the garment. Another known product includes a coated textile sock with anti-bubbles formed by an elastic or knitted fabric having an intertwining or integration of fibers, the textile having a first and second surface opposites that correspond to an inner surface of the sock and an outer surface of the sock, respectively. The textile includes silicone applied to the first surface and the silicone being cured, the silicone being applied and cured in such a way that the fibers of the textiles are at least partially coated, and the textile is porous.

The above-referenced products do not reveal properties related to skin health product and not even in settings that can be used in multiple parts of the body with comfort and safety. Further, the known products do not provide sufficient means of protection and relief from pain or injury. Further, no none of the known products provide users a simple function to make the socks not move.

SUMMARY OF THE INVENTION

The invention provides a wearable liquid silicone rubber product that overcomes the hereinafore-mentioned disadvantages of the heretofore-known devices and methods of this general type and that provides a product that can serve as an accessory, trim, protective product, specifically to offer comfort, protection, safety for therapeutic and beauty treatments. The present invention can be used on different parts of the body, with perfect adhesion, with high flexibility and elasticity adapting to different limb sizes and body shapes, respecting the differences of each individual and their movements, without displacement of the object. The objects are presented in configurations applied to gloves, socks, insoles, sleeves, hot and cold compresses, knee pads, elbow pads, among other objects, being made with a specific LSR. This specific silicone, in addition to being recognized as a hypoallergenic material, it is also antifungal.

For the objects to be produced, silicone is injected into molds, which when solidified/cured, transforms on specific objects and on some of these objects a gel is inserted in strategic parts. Said gel can be cooled or heated, where the object is used as compress for pain relief and muscle rehabilitation.

Those known products may have strong compressive properties, but they do not attend to the issue of flexibility in the joints of parts of the body of users where they are used, such as the knees, elbows, fingers etc., where limbs need be bent and when there is a compression of the place. Specifically, these known products are uncomfortable, painful, and uncomfortable to many users.

One of the main advantages of the present invention relates to the comfort, mobility, convenience to users when used or inserted on parts of the user's body. Further, the present invention provides an LSR product with specifically configured pleats thereon, thereby allowing expansion and varying of size in order to suit different users. The present invention also enables use as a sleeve with LSR that offers a total adhesion to the skin, avoiding displacement with the introduction innovative pleating, ruffle, that enables bending the joints where applied.

Another advantage is that the object can be heated or cooled down before use, since some of the objects receive the gel sheltered between the walls of the cured silicone thus offering analgesic care in the treatment of muscle pain and rehabilitation.

Another advantage of the objects introduced here as new, because they are made with LSR, offer a special protection between the apparatus worn by the user and the skin. It is known that the friction between devices used by users (such as in sports, wearing social shoes, etc.) when in contact with the skin, they provoke irritation, blisters and injuries to users' skin causing pain, limiting, and even preventing users from perform your assignments. However, one of the properties of LSR is its adhesion to the skin, therefore, innovative objects are made with liquid silicone rubber, form a protective layer acting as a second skin fully adherent to the user avoiding friction caused by direct skin contact with the apparatuses. This prevents the consequences caused by friction, such as blisters, corns, and other injuries, offering comfort and protection, and providing users the ability to perform better in their physical activities.

As such, the present invention can be applied to hot/cold compresses, may include pleats/ruffles, knee, and elbow pads and/or pleats combined with smooth silicones or with massage points, inserted in products that work like gloves and socks. Additionally, the present invention can utilize reinforcements combined with ruffles and perforations for skin breathing, preventing accumulation of sweat, particularly in gloves and socks. Further, smooth silicone with portions pleats/ruffles in strategic parts of the body, e.g., joints for mobility and adaptation to the size of the user. In other words, the new applications achieved may be made available in objects with various characteristics, together or separately.

The products already existing require immobility on the part of the user during the use. However, the objects shown here as new allow, during use, the full mobility of the user. This is because, in addition to the LSR being pliable and elastic, the addition of ruffle/pleats in the product allows flexion of the joint and also adaptation to the user size, thus allowing the user to make use of the limb (arm, leg, etc.) without being restricted to movements.

With the foregoing and other objects in view, there is provided, in accordance with the invention, a liquid silicone rubber product having a cured liquid silicone rubber ("LSR") body having an outer surface, an inner surface opposing the outer surface, a first end, a second end opposing the first end, a non-biased body length separating the first and second ends of the cured silicone body, a pre-formed pleated portion disposed circumferentially along the body length and operably configured to enable selective and elastically biased adjustment of the non-biased body length, non-pleated portions of the LSR body forming a smooth surface of the outer surface of the LSR body and flanking the pleated portion, forming a sleeve shape with at least one enclosed opening and a sleeve channel for receiving a user's limb and defined by the inner surface of the LSR body, and defining a plurality of perforations thereon, disposed on the non-pleated portions of the LSR body that span through the LSR body.

In accordance with another feature, an embodiment of the present invention includes the pleated portion having at least two pleated portions each separated by a non-pleated portion of the LSR body.

In accordance with yet another feature, an embodiment of the present invention also includes each of the at least two pleated portions having a plurality of folded sections of the LSR body each forming rounded portions of the outer surface of the LSR body.

In accordance with a further feature, an embodiment of the present invention also includes the rounded portions of the outer surface of the LSR body having an approximate 1 mm radius of curvature.

In accordance with a further feature of the present invention, the LSR body has a uniform non-biased thickness of approximately 1 mm. Further, the plurality of perforations are each of a uniform non-biased diameter of approximately 2 mm.

In accordance with yet another feature, an embodiment of the present invention also includes the plurality of perforations are each of a uniform non-biased diameter ranging from 0.5-2 times a uniform non-biased thickness of the LSR body.

In accordance with an additional feature, an embodiment of the present invention also includes the plurality of perforations disposed in a tightly spaced configuration not exceeding 25 mm with respect to one another.

In accordance with a further feature of the present invention, the LSR body is of anti-fungal silicone rubber material having an elongation at break ranging from 800-1100% of its non-biased body length.

In accordance with an additional feature, an embodiment of the present invention also includes a bottom surface of the LSR body, an upper surface of the LSR body opposing the bottom surface of the LSR body, and a plurality of longitudinally oriented pre-formed pleated portions and with one of the plurality of longitudinally oriented pre-formed pleated portions extending from the at least one enclosed opening and terminating at the first end.

In accordance with a further feature of the present invention, the LSR body further comprises at least one reinforced section disposed along the body length, disposed proximal to the second end of the LSR body, and having a reinforcement thickness at least twice a uniform non-biased thickness of the LSR body.

In accordance with an additional feature, an embodiment of the present invention also includes a bottom surface of the LSR body, an upper surface of the LSR body opposing the bottom surface of the LSR body, and a plurality of longitudinally oriented pre-formed openings and with one of the plurality of longitudinally oriented pre-formed openings extending from the at least one enclosed opening and terminating at the first end.

In accordance with a further feature of the present invention, a plurality of massaging points is disclosed that extends outwardly from the inner surface of the LSR body and disposed along the body length.

In accordance with an additional feature, an embodiment of the present invention also includes a pouch formed on the LSR body, disposed along the body length, and containing gel inside of walls forming the LSR body.

Although the invention is illustrated and described herein as embodied in a wearable liquid silicone rubber product, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time. Also, for purposes of description herein, the terms "upper", "lower", "left," "rear," "right," "front," "vertical," "horizontal," and derivatives thereof relate to the invention as oriented in the figures and is not to be construed as limiting any feature to be a particular orientation, as said orientation may be changed based on the user's perspective of the device. Furthermore, there is no intention to be bound by any expressed or implied theory presented in the preceding technical field, background, brief summary or the following detailed description.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the product and/or spanning from the upper end of the product to a lower end of the product.

DESCRIPTION OF THE FIGURES

For a better and adequate understanding of the utility model, it becomes described below with the help of the attached figures, in which we will describe each of them.

FIG. 4 reveals a front view of the object in a leg (A) where it is possible to observe the portion pleated/pleated (C) on one unbent (A) leg.

FIG. 5 reveals a side view of the object in a leg (A) where it is possible to observe the portion pleated/pleated (C) on one unbent (A) leg.

FIG. 6 refers to a new layout, in format of sleeve (sleeve) (F), having your body completely ruffle/ruffle (C), for use on shin, thigh, upper arm and forearm and with gel insert (B) for use as cooled or heated pads.

FIG. 10 shows a wristband for the wrist of the sleeve type (sleeve), with pleated material (C), reinforcement (E) and with gel insert (B) for use as cooled or heated pads.

FIG. 14 reveals smooth silicone socks/gloves (S) that can be used with the insertion of cosmetic or medicated creams/gels/ointments. Creams/gels/ointments have their active ingredients potentiated since the object will not be able to easily evaporation inside the silicone sock or glove.

FIG. 15 reveals socks/gloves made of silicone with massaging points (U) that are used for massaging the body portion to which they are disposed.

FIGS. 16-17 depict a wearable liquid silicone rubber product with exemplary dimensions in mm in an elevational side view and a top plan view, respectively, in accordance with one embodiment of the present invention.

FIG. 18 depicts section A-A in FIG. 17 in accordance with one embodiment of the present invention.

FIG. 19 depicts detail B FIG. 18 in accordance with one embodiment of the present invention.

FIG. 20 depicts a perspective view of a wearable liquid silicone rubber product along with a close-up view of detail C in accordance with one embodiment of the present invention.

FIGS. 25-26 depict a wearable liquid silicone rubber product with exemplary dimensions in mm in an elevational side view and a top plan view, respectively, in accordance with one embodiment of the present invention.

FIG. 27 depicts section A-A in FIG. 26 in accordance with one embodiment of the present invention.

FIG. 28 depicts a perspective view of the product depicted in FIG. 25 in accordance with one embodiment of the present invention.

FIG. 29 depicts a close-up view of detail C in FIG. 27 in accordance with one embodiment of the present invention.

Figure 1:
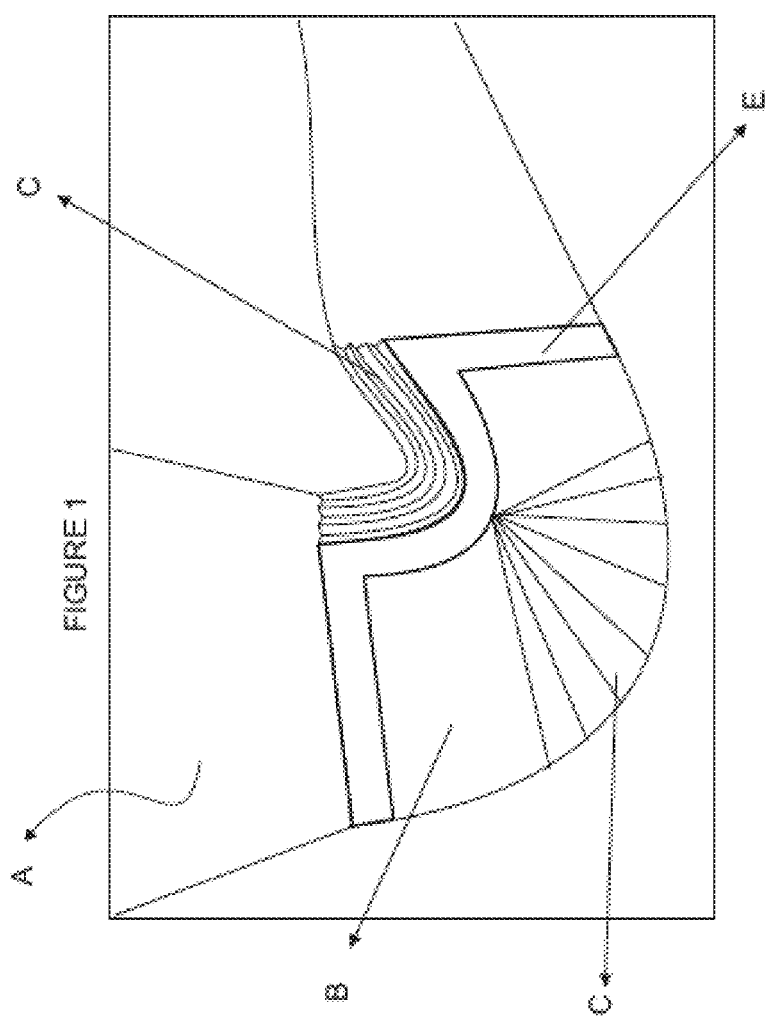
FIG. 1 illustrates the wearable LSR product added to the leg (A) of a person, more specifically to the knee and it is possible note that when bending the knee, the portions pleats/ruffles (C) of the objects open so that the movements can be performed as well as to suit the various body proportions. The therapeutic portion, form a pouch (B) on the objects, which contain a gel. The tracks (E) strengthen the attachment to the skin helping objects to stick to the body, even though the silicone itself is already highly adherent, avoiding slipping so that they do not come out of the place.
Figure 2:
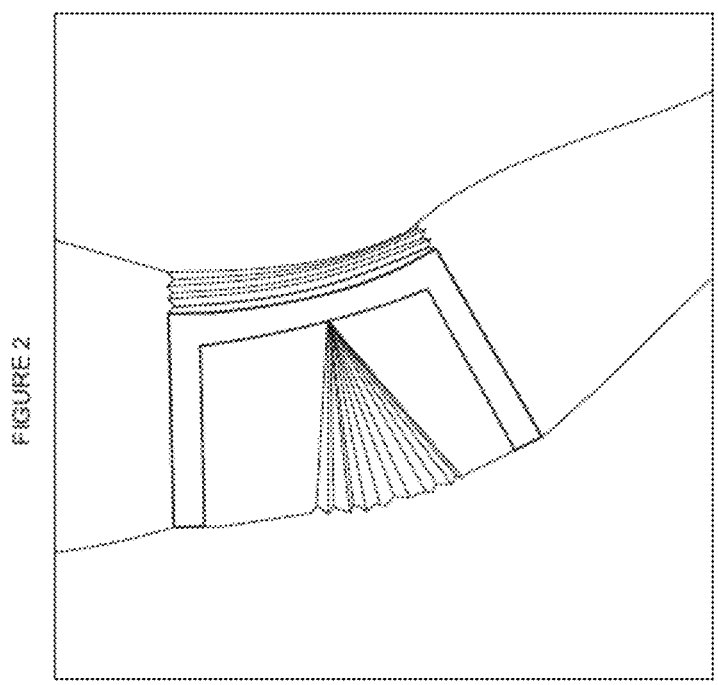
FIG. 2 shows the object again added to a knee where the person has not fully bent the leg.
Figure 3:
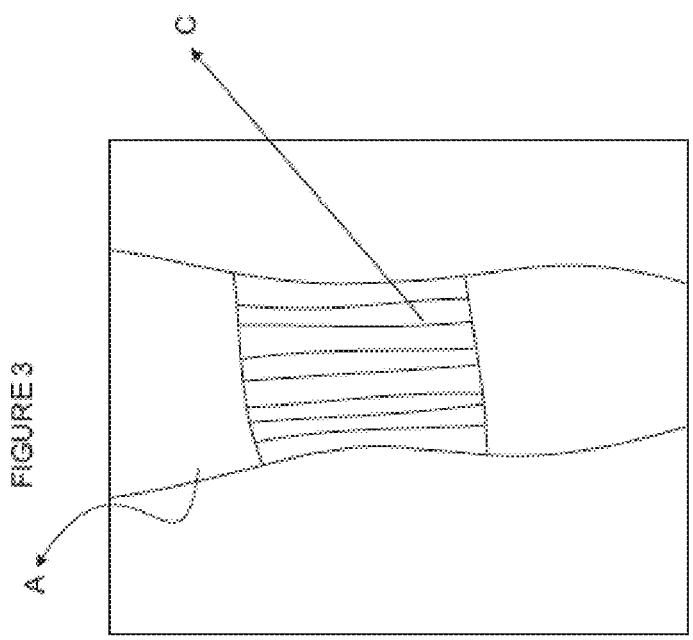
FIG. 3 reveals a rear view of the object in a leg where you can see another point ruffle/ruffle (C) fitted to the back of a leg (A).
Figure 7:
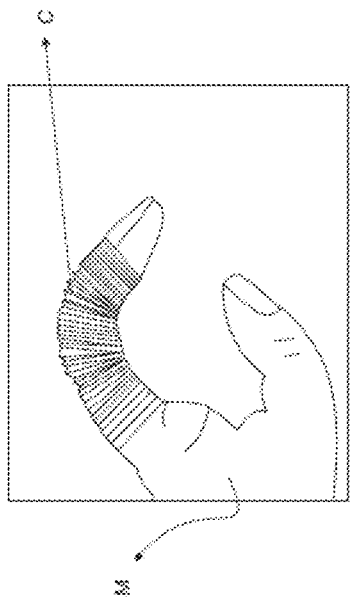
FIG. 7 shows a finger (M) where a sleeve (sleeve) (F) that has portions pleats/ruffles (C) to facilitate movement and to fit to size, as well as FIGS. 8 and 9 represent front and rear views, respectively, of the hose (F) with pleated/pleated body (C) horizontally (FIG. 8) and vertically (FIG. 9) and with gel insert (B) for use as cooled or heated compresses.
Figure 8:
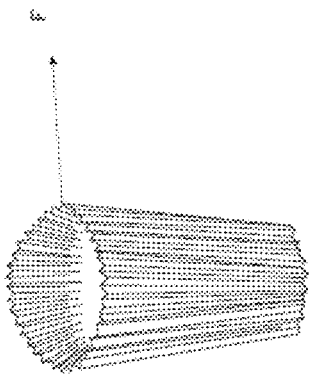
Figure 9:
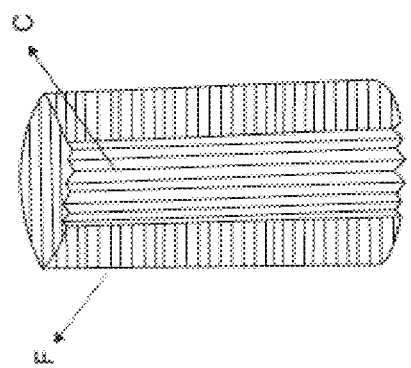
Figure 8:
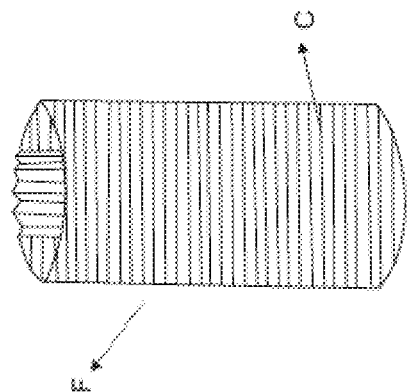
Figure 11:
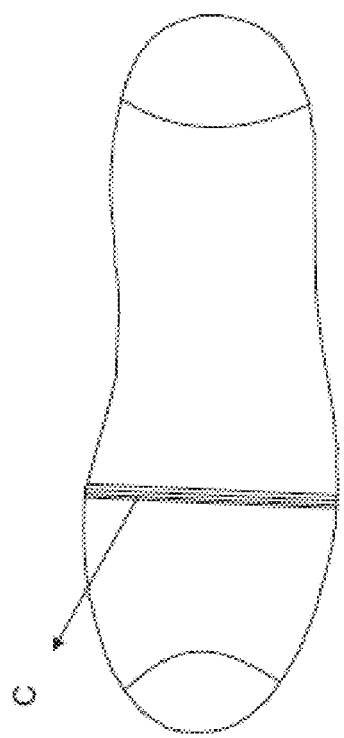
FIG. 11 shows the sole of a sock or an insole, where it is possible to verify that the ruffle/ruffle (C) can be presented in parts objects.
Figure 13:
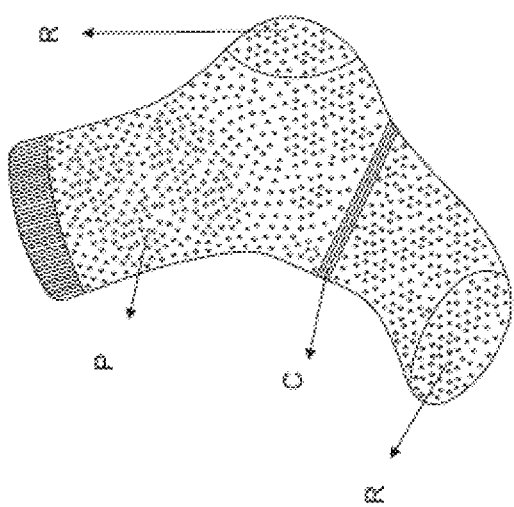
FIG. 13 represents a comfort sock with perforations (P) to facilitate skin breathing, sections reinforced (R) in the toes and heel, also having a pleated/pleated portion (C).
Figure 12:
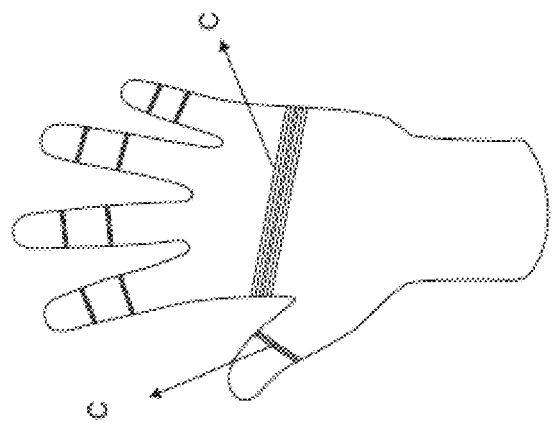
FIG. 12 illustrates a glove, in which the pleats/ruffles (C) present in the knuckles of the fingers and in the Palm.
Figure 21:
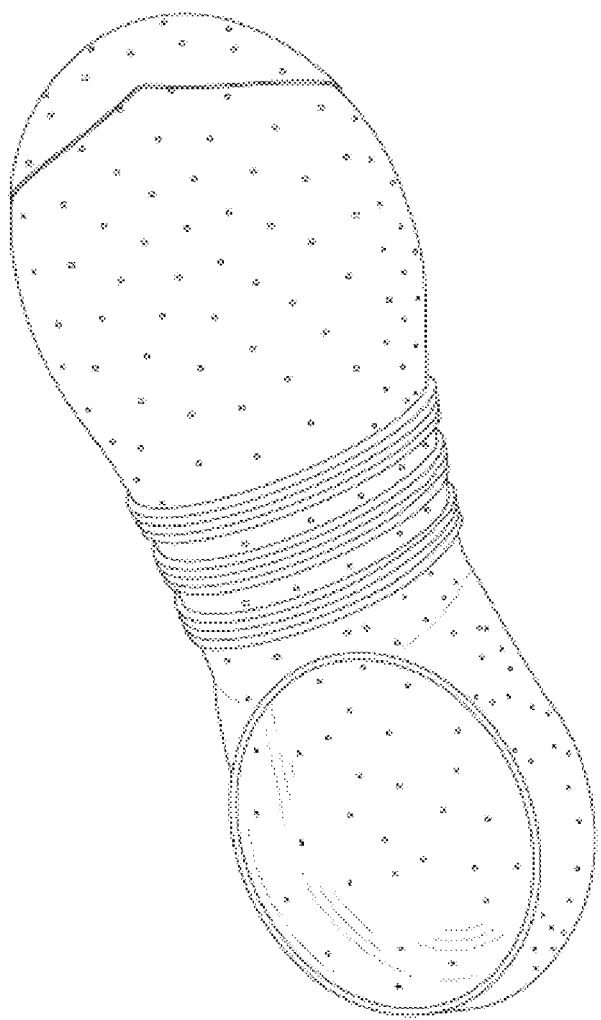
FIGS. 21-24 depict various views of a wearable liquid silicone rubber product in accordance with one embodiment of the present invention.
Figure 22:
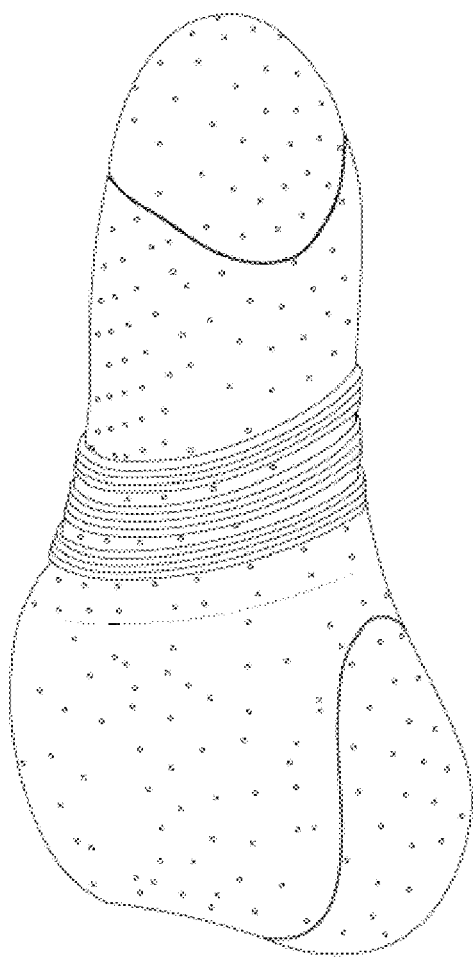
Figure 23:
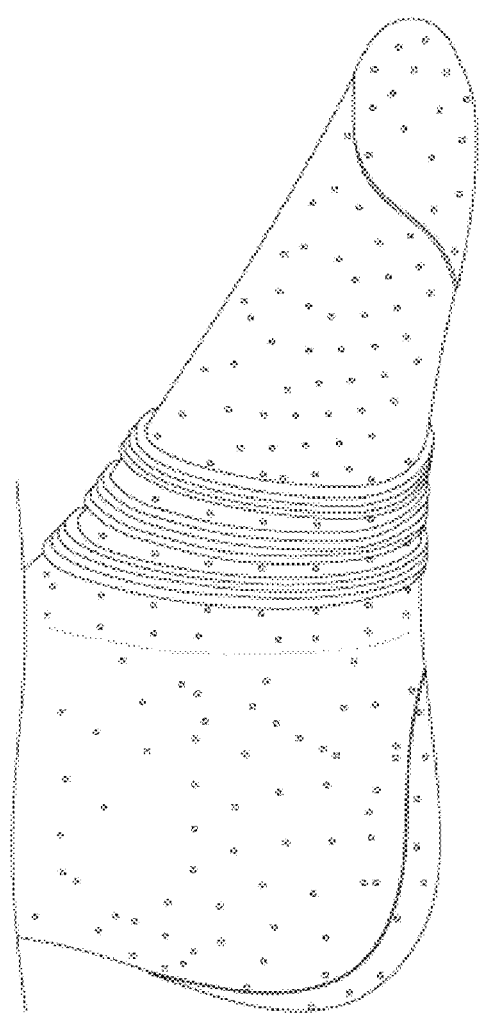
Figure 24:
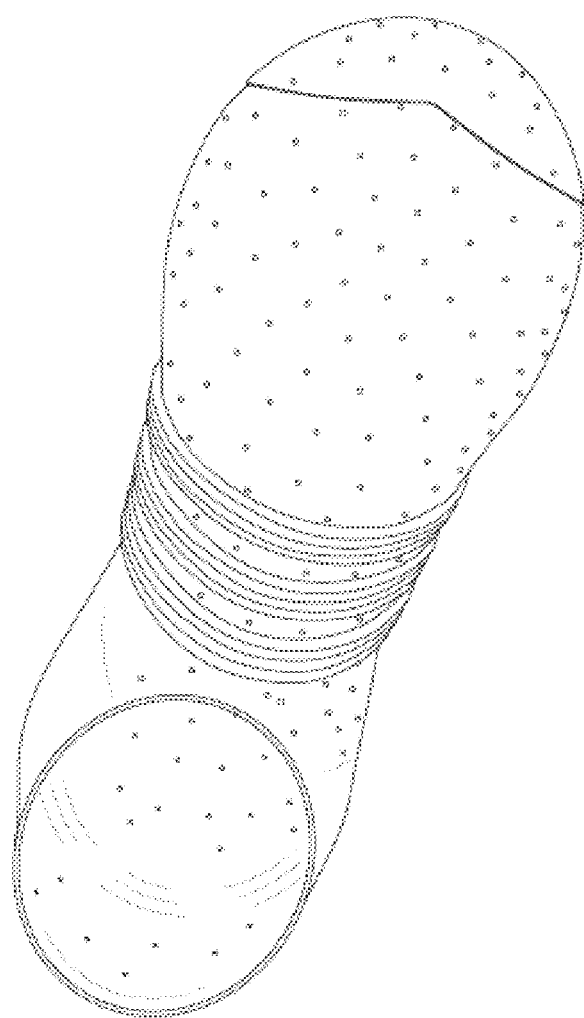

For this purpose, the perforations (P) facilitate breathing of the skin so that there is no excessive moisture; the sections reinforced (R) complement the material for greater comfort at strategic points; the pleated/pleated area (C) receives a strip of pleated material adapting the objects to different sizes of users, as well as to allow movement when used on joints; the objects in smooth or pleated silicone with closed finish, type socks and gloves, can receive creams/gels/ointments for use moisturizing or therapeutic and as silicone does not absorb the products applied and being anti-fungal, the treatment is more effective and safer; the massaging points (U) are used to massage the body portion in which are willing.

DETAILED DESCRIPTION

In accordance with figures the objects obtained are comfortable, adaptable, and made with liquid silicone rubber (LSR), which is used as an FDA and Anvisa approved material, and is safe to use objects that have direct contact with the human skin. The LSR is cured in molds, with or without the insertion of gel, it can be cooled or heated. These molds idealize objects that can be used for products related to various physical activities or exercises, for walking, resting, practicing sports, treatments/physical rehabilitation, skin care, etc., in the most diverse parts of the body, providing comfort, protection, care and rehabilitation of the skin and musculature.

Used in cases where there is direct contact, of any type of device, sporty or not, with the skin, producing friction, the objects prevent friction arising movements avoiding their harmful consequences. The objects provide a barrier, creating a second skin, that prevents direct skin contact with the apparatus used (such as social and sports shoes, appliances exercises, etc.) avoiding blisters, corns, and other injuries caused by friction.

Another function of the present invention is to help in the healing of cuts, treatment of dryness or cracks in the skin and pain relief, muscle treatment, etc. For this the smooth silicone objects (S), with or without elements ruffles/ruffles (C). The skin can receive products medicinal, therapeutic, or cosmetic, and the action moisturizing or healing will be more effective, as the silicone does not absorb products inserted into the skin preserving its properties.

Another function of the present invention includes perforations (P) in socks, gloves, and other objects that allow breathing of the skin. Therefore, said perforations (P) allow ventilation that prevents moisture and accumulation of sweat and its consequences.

Further, pleated/ruffled portion (C) on the product has two functions, one being for mobility, when the part pleated/folded opens so that the movement, of the joints, can be done without hindrance, another is when the pleated/folded portion opens for object to fit to the size of the users. Therefore, the portion pleated/folded is a novelty in these types of objects making them more comfortable and efficient. In the case of sleeve (sleeve) (F), for use on the fingers pleated/folded, to allow movement, incorporates the entire length of the object due to two joints being close to each other, and this sleeve (sleeve) it can also be adapted to other parts of the body.

The LSR products are made with cured liquid silicone rubber and may include reinforcement thickness (E) that adheres to the skin, adapting to the body part without leaving the place during use.

At strategic points of the object, where there is greater friction, sections are reinforced/thick (R) for greater protection and comfort of users.

Socks and gloves have cracks in the soles and palms with anti-slip function, allowing the user to walk without slipping and handling objects without them they slip from one's hands.

Liquid silicone rubber (LSR) used has good stability resisting high and low temperatures, it has superior compatibility with human tissue and fluid, is resistant to bacteria/microbes/fungi, odorless, tasteless and can be formulated to meet sanitary requirements, it can also be sterilized with a variety of methods, it is extremely resistant, has good durability (tensile strength and wear resistance) and has excellent flexibility. In one embodiment, the LSR material is of anti-fungal silicone rubber material having an elongation at break ranging from 800-1100% of its non-biased body length. More specifically and preferably, the LSR material also has the following property ranges: 3,000-23,000 (cps, mixed viscosity), 1.06-1.08 (g/cc, specific gravity), 25-26 (specific volume cu. in./lb.), 4-5 hours cure time, 00-33 (shore A hardness), 200-500 (psi, tensile strength), 10-25 (psi, 100% modulus), and −65° F.-450° F. (useful temperature range). The color of the cured LSR may be beneficially transparent or opaque (as depicted best in FIGS. 21-24).

With reference to FIGS. 16-20, the liquid silicone rubber product 1600 includes a cured liquid silicone rubber body 1602 having an outer surface 1608, an inner surface 1700 opposing the outer surface 1608, a first end 1604, a second end 1606 opposing the first end 1604, and a non-biased body length (i.e., its length without any external forces applied thereto or its static length) separating the first and second ends of the cured silicone body 1602. The LSR body 1602 has elasticity, but the product 1600 beneficiary includes a pre-formed pleated portion 1610 disposed circumferentially around the product 1600 and along the body length that is/are operably configured to enable selective and elastically biased adjustment of the non-biased body length. Specifically, the pre-formed pleated portion 1610 enables selective adjustment longitudinally to change the product, for example, from a length of 246 mm to 258 mm, or from a size 37 (EU) foot to a size 41 (EU) foot.

In one embodiment, the pleated portion includes at least two (but preferably three to four) pleated portions each separated by a non-pleated portion of the LSR body 1602. Each of the at least two pleated portions also includes a plurality of folded sections 1900*a-n* of the LSR body 1602 each forming rounded portions of the outer surface 1608 of the LSR body 1602. Exemplary but preferable dimensions of the pleated portion and the plurality of folded sections 1900*a-n* are depicted in the figures. Specifically, the rounded portions of the outer surface 1608 of the LSR body 1602 have an approximate 1 mm radius of curvature, thereby providing a configuration that does not interfere with the operability of a shoe surrounding the product (when utilized on a user's foot) and provides comfort to the user. Each of the pleated portions may span approximately 8-10 mm and each of the plurality of folded sections 1900*a-n* may form a length of approximately 2 mm to minimize interference and achieve the benefits of the product discussed herein.

The non-pleated portions of the LSR body 1602 form a smooth surface of the outer surface 1608 of the LSR body 1602 and flank the pleated portion. A smooth surface may also be formed on the pre-formed pleated portion 1610 and the inner surface 1700 of the LSR body 1602, thereby providing a comfortable and conforming surface for the user. The LSR body 1602 may form a sleeve shape, e.g., an elongated structure with at least one opening (e.g., a sock or a glove). The product 1600 may also include at least one enclosed opening 1702 and a sleeve channel 1800 for receiving a user's limb and defined by the inner surface 1700 of the LSR body 1602.

The product 1600 may also beneficially define a plurality of perforations 1612*a-n* thereon and disposed on the non-pleated portions of the LSR body 1602 and that span through the LSR body 1602, i.e., fluidly coupling the sleeve channel 1800 to the outer ambient environment. In one embodiment, the LSR body 1602 has a uniform non-biased thickness of approximately 1 mm to provide comfort of the user, mobility and utilization of the user's limb covered by the product, and effectiveness of the product to overcome the disadvantages associated with known products.

Specifically, the plurality of perforations 1612*a-n* may each be of a uniform or non-uniform non-biased diameter of approximately 2 mm. The plurality of perforations 1612*a-n* may also each be of a uniform non-biased diameter ranging from 0.5-2 times a uniform non-biased thickness of the LSR body 1602. In one embodiment, the plurality of perforations 1612*a-n* are disposed in a tightly spaced configuration not exceeding 25 mm with respect to one another to achieve the benefits of the product discussed herein.

In one embodiment and as specifically shown in FIG. 17, the LSR body 1602 includes a bottom surface 1614 of the LSR body 1602, an upper surface 1616 of the LSR body 1602 opposing the bottom surface 1614 of the LSR body 1602, and a plurality of longitudinally oriented pre-formed pleated portions 1704a-n and with one of the plurality of longitudinally oriented pre-formed pleated portions 1704a-n extending (in some embodiments, continuously) from the at least one enclosed opening 1702 and terminating at the first end 1604. Said another way and as also depicted in FIG. 17, a plurality of longitudinally oriented pre-formed openings and with one of the plurality of longitudinally oriented pre-formed openings extending from the at least one enclosed opening 1702 and terminating at the first end 1604. The plurality of longitudinally oriented pre-formed openings may be formed by the pleated portions 1704a-n or by forming slits in the LSR body 1602 that span through the thickness thereon.

In additional embodiments, the LSR body 1602 includes at least one reinforced section 1616 disposed along the body length, disposed proximal (i.e., at or near, within 10% of the overall length) to the second end 1606 of the LSR body 1602, and having a reinforcement thickness at least twice a uniform non-biased thickness of the LSR body 1602. The reinforcement thickness may also be uniformly distributed.

As discussed herein, a plurality of massaging points may also be defined on the product and extending outwardly from the inner surface 1700 of the LSR body 1602 and disposed along the body length. Furthermore, a pouch may be formed on the LSR body 1602, disposed along the body length, and containing gel inside of walls forming the LSR body 1602. Additionally, a plurality of strips disposed along the first and second ends of the LSR body 1602 and reinforce the product.

With reference to FIGS. 25-29, another embodiment of an LSR body 2500 is depicted, wherein the reinforced sections 2502 are beneficially moved and configured to achieve the benefits of the product discussed herein.

Figure 30:
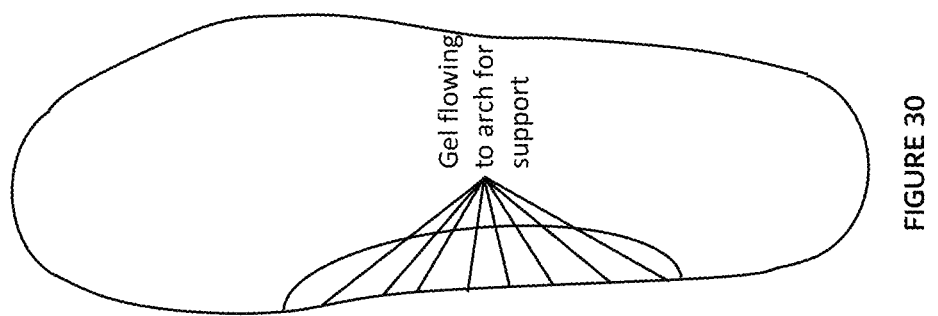
FIG. 30 depicts the sole of a sock or an insole with gel supporting the arch in accordance with one embodiment of the present invention.

As can be seen in FIG. 30, the liquid silicone rubber (LSR) product includes a cured LSR body formed as a sole for a sock or shoe, having a left side forming an arch portion of the sole, having a right side opposing the left side of the sole, having an outer surface, an inner surface opposing the outer surface, a first end, a second end opposing the first end, a body length separating the first and second ends of the cured silicone body, having a perimeter edge interposed between the body length, and with a gel injected into the LSR body at the perimeter edge and the left side and spanning in direction toward the right side of the LSR body for support of the user's foot arch. Additionally, FIG. 30 can be seen with the gel tapering in the direction toward the right side of the LSR body.

The invention claimed is:

1. A liquid silicone rubber (LSR) product comprising:
a cured silicone body:
    having an outer surface, an inner surface opposing the outer surface, a first end, and a second end opposing the first end;
    having a non-biased body length separating the first and second ends of the cured silicone body;
    having at least one reinforced section disposed along the non-biased body length, disposed on the outer surface and proximal to the second end of the cured silicone body, and having a reinforcement thickness greater than a non-biased thickness of the cured silicone body;
    having a pre-formed pleated portion disposed circumferentially along the body length and operably configured to enable selective and elastically biased adjustment of the non-biased body length;
    having non-pleated portions forming a smooth surface of the outer surface of the cured silicone body and flanking the pleated portion; and
    forming a sleeve shape with at least one enclosed opening and a sleeve channel for receiving a user's limb and defined by the inner surface of the cured silicone body.

2. A liquid silicone rubber (LSR) product comprising:
a cured liquid silicone rubber ("LSR") body formed as a sole for a sock or shoe, having a left side forming an arch portion of the sole, having a right side opposing the left side of the sole, having an outer surface, an inner surface opposing the outer surface, a first end, a second end opposing the first end, a body length separating the first and second ends of the cured silicone body, having a perimeter edge interposed between the body length, and with a gel injected into the LSR body at the perimeter edge and the left side and spanning in direction toward the right side of the LSR body.

3. The liquid silicone rubber (LSR) product according to claim 2, wherein the gel tapers in the direction toward the right side of the LSR body.

* * * * *